United States Patent
Mourey et al.

(10) Patent No.: US 10,520,440 B2
(45) Date of Patent: Dec. 31, 2019

(54) GAS-PHASE DELIVERY SYSTEM FOR MOLECULE SENSING APPARATUS

(75) Inventors: Devin Alexander Mourey, Albany, OR (US); James William Stasiak, Lebanon, OR (US); James Elmer Abbott, Jr., Albany, OR (US); Zhiyong Li, Foster City, CA (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 1020 days.

(21) Appl. No.: 14/377,524

(22) PCT Filed: Feb. 8, 2012

(86) PCT No.: PCT/US2012/024371
§ 371 (c)(1),
(2), (4) Date: Aug. 8, 2014

(87) PCT Pub. No.: WO2013/119228
PCT Pub. Date: Aug. 15, 2013

(65) Prior Publication Data
US 2015/0330902 A1    Nov. 19, 2015

(51) Int. Cl.
*G01J 3/44* (2006.01)
*G01N 21/65* (2006.01)

(52) U.S. Cl.
CPC ..... *G01N 21/658* (2013.01); *G01N 2201/068* (2013.01); *G01N 2201/06113* (2013.01)

(58) Field of Classification Search
CPC ............... G01N 21/65; G01N 21/658; G01N 2021/656; G01N 2201/06113; G01N 2201/068; G01J 3/02; G01J 3/44

USPC ............................................. 356/301, 72–73
See application file for complete search history.

(56) References Cited

U.S. PATENT DOCUMENTS

| | | | |
|---|---|---|---|
| 6,947,132 B1 * | 9/2005 | Boss | G01J 3/44 356/301 |
| 7,898,658 B2 | 3/2011 | Moskovits et al. | |
| 2007/0070341 A1 | 3/2007 | Wang | |
| 2007/0086002 A1 | 4/2007 | Islam et al. | |
| 2007/0155020 A1 | 7/2007 | Su et al. | |
| 2007/0229817 A1 * | 10/2007 | Wang | G01N 21/658 356/301 |
| 2007/0252983 A1 | 11/2007 | Tong et al. | |
| 2008/0074662 A1 * | 3/2008 | Gu | G01N 21/658 356/301 |
| 2009/0098344 A1 | 4/2009 | Tomaru | |

(Continued)

FOREIGN PATENT DOCUMENTS

WO    WO-2011093876    8/2011

OTHER PUBLICATIONS

Biggs, et al; Surface-Enhanced Raman Spectroscopy of Benzenethiol Absorbed from the Gas Phase onto Silver Film over Nanosphere Surfaces; Determination of the Sticking Probability and Detection Limit Time; ACS Publications; The Journal of Physical Chemist; J. Phys. Chem. A 2009,.

*Primary Examiner* — Abdullahi Nur
(74) *Attorney, Agent, or Firm* — HP Inc. Patent Department

(57) ABSTRACT

Molecule sensing apparatus. The apparatus has first and second chambers, an input port extending into the first chamber, a fluid channel extending from the first chamber to the second chamber, and a surface-enhanced substrate in the second chamber.

20 Claims, 10 Drawing Sheets

(56) References Cited

U.S. PATENT DOCUMENTS

| | | | |
|---|---|---|---|
| 2010/0081260 A1* | 4/2010 | Chen | C23C 16/22 |
| | | | 438/478 |
| 2010/0315629 A1* | 12/2010 | Knopp | G01J 3/02 |
| | | | 356/301 |
| 2011/0116089 A1 | 5/2011 | Schmidt et al. | |
| 2013/0021605 A1* | 1/2013 | Yi | G01N 21/658 |
| | | | 356/301 |

* cited by examiner

GAS-PHASE DELIVERY SYSTEM FOR MOLECULE SENSING APPARATUS

BACKGROUND

Spectroscopy refers to determining the nature of a substance by measuring a parameter of energy emitted by the substance. For example, if a laser beam is scattered off of a substance, some of the photons in the scattered beam will have a different wavelength than those in the incident beam. This results from an exchange of energy between the incident photons and the molecules of the substance and is called the Raman Effect. The substance can be identified by measuring how much the wavelength has shifted. The Raman Effect can be enhanced by adsorbing molecules of the substance onto a rough metal surface and then exposing them to the incident laser beam. This technique is referred to as surface-enhanced Raman spectroscopy (SERS). The enhancement factor is so high—as much as $10^{11}$—that individual molecules of the substance can be identified. A suitable surface may be prepared by forming tiny projections called nanofingers on a silicon substrate and depositing a thin coating of metal such as gold or silver on the nanofingers. Then, when the nanofingers are exposed to a liquid, the liquid flows between the nanofingers and capillary action causes them to bend toward each other, trapping individual molecules of the liquid. The nanofingers may be thought of as tiny tweezers that hold individual molecules of the liquid up to the laser beam for analysis.

BRIEF DESCRIPTION OF THE DRAWINGS

The figures are not drawn to scale. They illustrate the disclosure by examples.

DETAILED DESCRIPTION

Figure 1:
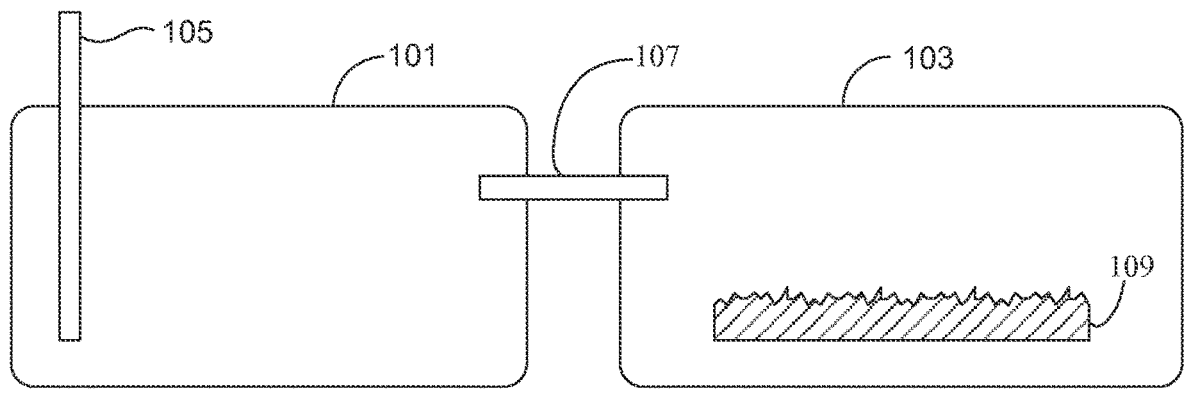
FIG. 1 is a schematic representation of an example of molecule sensing apparatus.

Illustrative examples and details are used in the drawings and in this description, but other configurations may exist and may suggest themselves. Parameters such as voltages, temperatures, dimensions, and component values are approximate. Terms of orientation such as up, down, top, and bottom are used only for convenience to indicate spatial relationships of components with respect to each other, and except as otherwise indicated, orientation with respect to external axes is not critical. For clarity, some known methods and structures have not been described in detail. Methods defined by the claims may comprise steps in addition to those listed, and except as indicated in the claims themselves the steps may be performed in another order than that given. Accordingly, the only limitations are imposed by the claims, not by the drawings or this description.

The systems and methods described herein may be implemented in various forms of hardware, software, firmware, special purpose processors, or a combination thereof. At least a portion thereof may be implemented as an application comprising program instructions that are tangibly embodied on one or more program storage devices such as hard disks, magnetic floppy disks, RAM, ROM, and CDROM, and executable by any device or machine comprising suitable architecture. Some or all of the instructions may be remotely stored and accessed through a communication facility; in one example, execution of remotely-accessed instructions may be referred to as cloud computing. Some of the constituent system components and process steps may be implemented in software, and therefore the connections between system modules or the logic flow of method steps may differ depending on the manner in which they are programmed.

SERS has been used to identify liquid analytes. For example, an analyte is adsorbed on a rough metal surface of a substrate and then is exposed to incident radiation such as a laser beam. As another example, nanofingers carried by a substrate controllably collapse (lean toward each other) in the presence of a liquid analyte, trapping minute quantities of the analyte as small as single molecules for exposure to incident radiation. SERS techniques such as these have been limited to liquid analytes, and accordingly the very high sensitivities afforded by SERS have not been adaptable to analytes not in liquid form. Many systems of interest would benefit from the capability to analyze solids and gases as well as liquids. Moreover, even with liquid analytes it has been difficult to avoid contamination that can convolute the SERS signal.

FIG. 1 gives an example of molecule sensing apparatus that includes a first chamber 101, a second chamber 103, an input port 105 extending into the first chamber, a fluid channel 107 extending from the first chamber to the second chamber, and a surface-enhanced substrate 109 in the second chamber.

Figure 2:
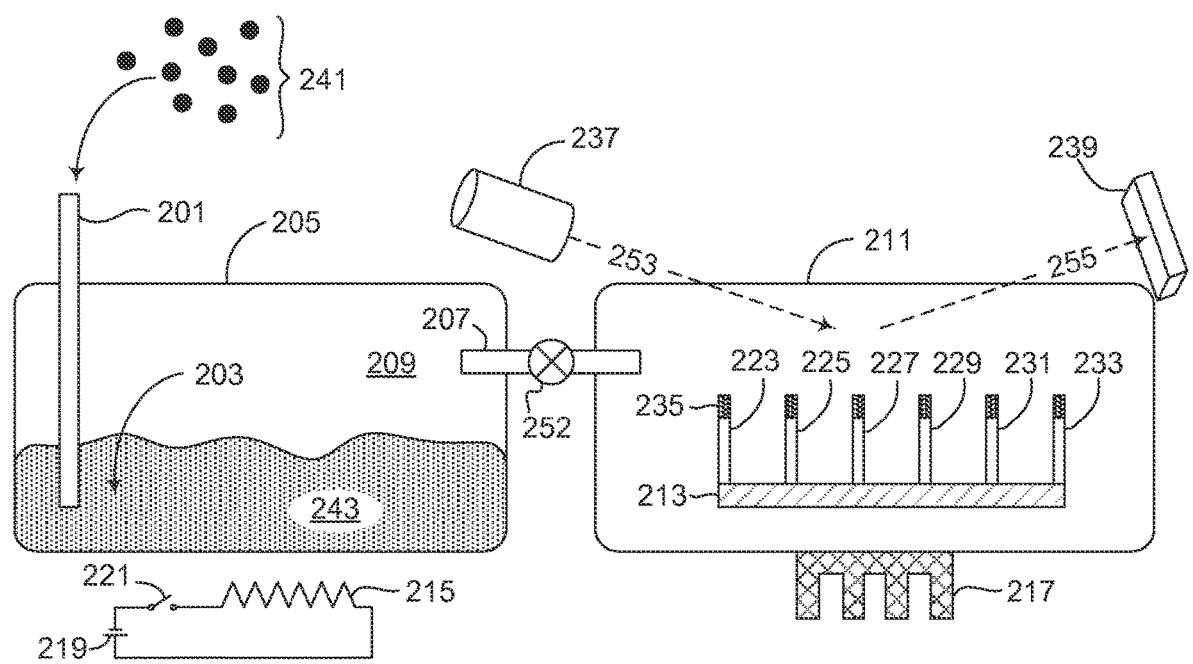
FIG. 2 is a schematic representation of an example of molecule sensing apparatus configured as SERS apparatus including a gas-phase analyte ready for mixing with a solvent.

FIG. 2 gives another example of molecule sensing apparatus. In this example the apparatus is configured as a surface-enhanced gas-phase Raman spectrometer. An input port 201 extends into a lower portion 203 of a first chamber 205. A fluid channel 207 extends from an upper portion 209 of the first chamber to a second chamber 211. A surface-enhanced substrate 213 is disposed in the second chamber.

A temperature differential may be maintained between the first chamber 205 and the second chamber 211, for example by a heat source such as a heating element 215 in thermal communication with the first chamber 205, or by a cooler such as a heat sink 217 in thermal communication with the second chamber 211, or by both a heat source and a cooler. In the example shown in FIG. 2, the heating element 215 is powered by a battery 219 in series with a switch 221, but other kinds of heat sources may be used. A refrigeration system or other cooler may be used in place of the heat sink 217.

In some examples the surface-enhanced substrate comprises a rough metal surface as shown in FIG. 1. In other examples such as that shown in FIG. 2, the surface-enhanced substrate may comprise a plurality of deformable projections such as nanofingers 223, 225, 227, 229, 231, and 233 spaced apart from each other by a distance over which capillary action of a fluid on the projections can deform the nanofingers toward one another. A tip of each nanofinger may comprise a metal surface such as the surface 235 of the nanofinger 223. Gold, silver, or another suitable metal may be used.

In the example of FIG. 2 the nanofingers are shown arranged in a linear pattern such that two nanofingers bend toward each other under the influence of capillary action, but the nanofingers may be disposed in an array and spaced such that capillary action causes three or more of the nanofingers to bend toward each other.

A radiation source such as a laser 237 may be directed toward the substrate. A radiation receiver such as a photo detector 239 is oriented to receive laser radiation scattered from the substrate. Elements such as optical filters and a light dispersion element, for example a grating, may be located in the optical path as will be discussed in more detail presently.

Figure 3A:
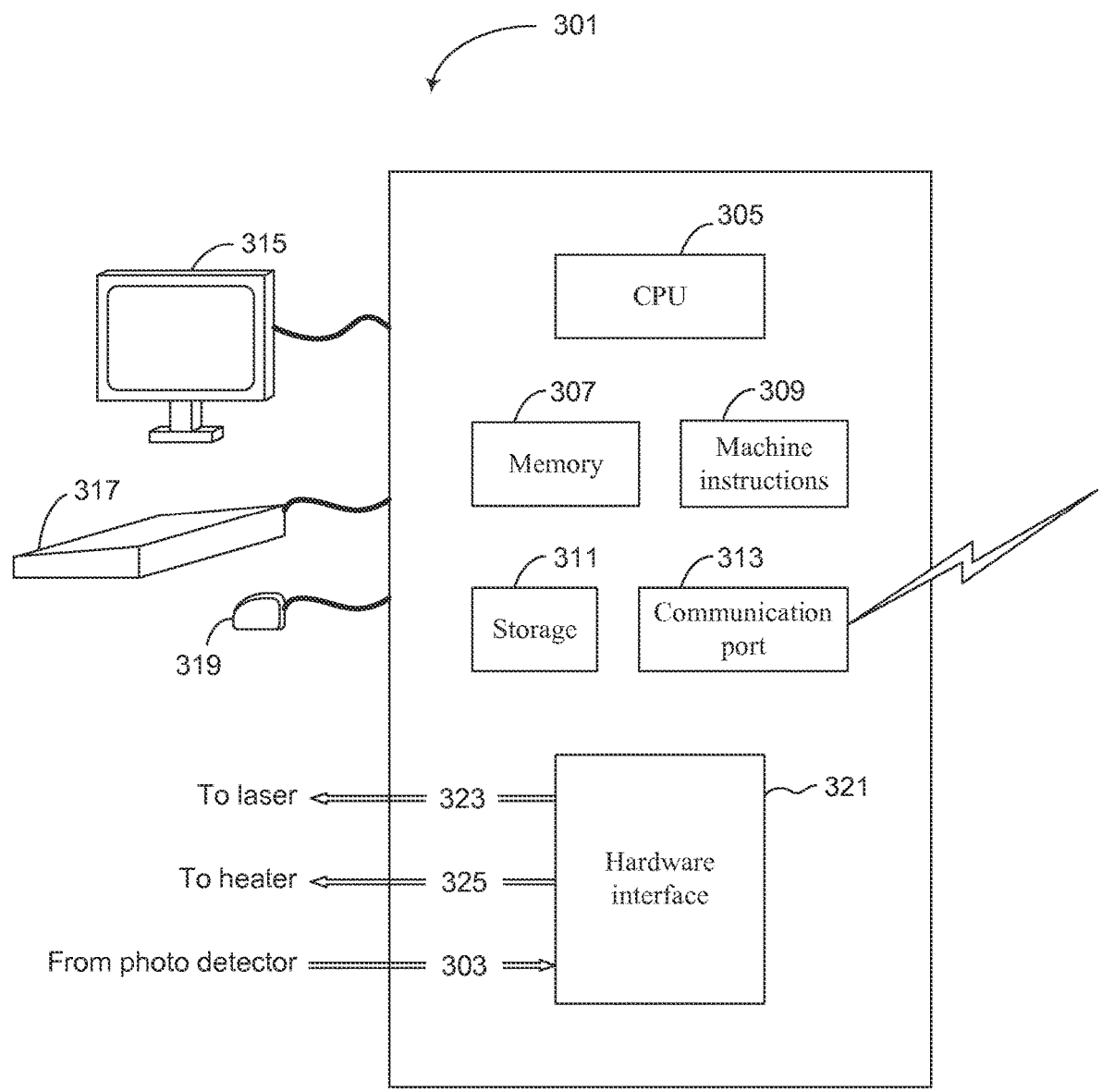
FIG. 3A is a block diagram of an example of a computer system configured to determine a spectrum of an analyte and compare the spectrum with known spectra to identify an analyte.

FIG. 3A gives an example of a computer (generally, 301) in electrical communication with the photo detector 239 as indicated by a communication line 303. The computer 301 may include one or more of a CPU 305, memory 307, machine instructions 309 that control the computer as described in more detail presently, storage 311 such as a hard disk or remotely-located storage, and a communication port 313 through which the computer can communicate with remote systems. Peripherals such as a visual display 315, a keyboard 317, and a pointing device 319 may be included. The machine instructions may be hard-wired or may be stored in a portion of the memory 307 or the storage 311, or they may be called through the communication port 313 from a remote location.

A hardware interface 321 may be used to facilitate electrical communication between the computer and the photocell. The computer may also control the laser 237 through a communication line 323 and the heater 215 through a communication line 325. The computer may control cooling of the second chamber, pressure in one or both chambers, or other physical parameters as desired.

Figure 3B:
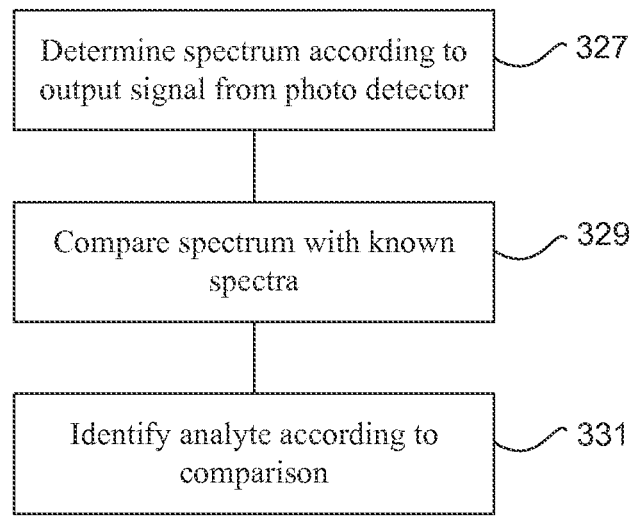
FIGS. 3B and 3C are flow charts depicting instructions in the computer system of FIG. 3A.

FIG. 3B gives an example of machine instructions that control the computer to determine (327) a spectrum according to an output signal from the photo detector. For example, such a spectrum may comprise a set of wavelengths at which the photocell gives an output together with the magnitude of the output at each such wavelength. The spectrum so obtained is then compared (329) with spectra of known substances to find a match and thereby identify (331) the analyte.

Figure 3C:
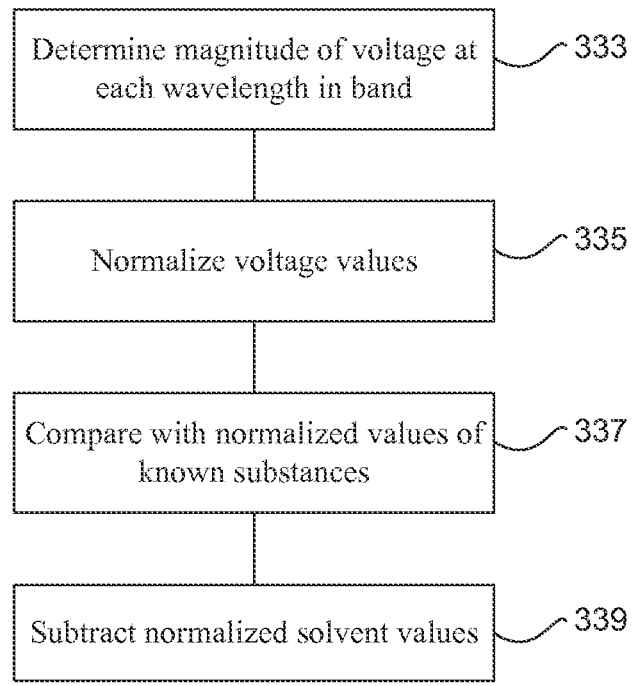

In the example of FIG. 3C the computer determines (333) the magnitude of a voltage output from the photocell at each wavelength within a band of wavelengths generally centered on the wavelength of the incident radiation. These voltage levels may then be normalized (335) to a predetermined range of values. The normalized values may be represented graphically or arranged in a table. The resulting graph or the values in the table may then be compared (337) with normalized values resulting from analyses of various known substances until a match is found. In some examples normalized voltage values for the solvent may be subtracted (339) to prevent the solvent from interfering with the analysis.

Referring again to FIG. 2, the spectrometer is shown ready for use in identifying an unknown analyte 241. A liquid solvent 243 has been disposed in the lower portion 203 of the first chamber 205, covering a lower extremity of the input port 201. A solvent having high vapor pressure, for example alcohol or toluene, may be used.

Figure 4:
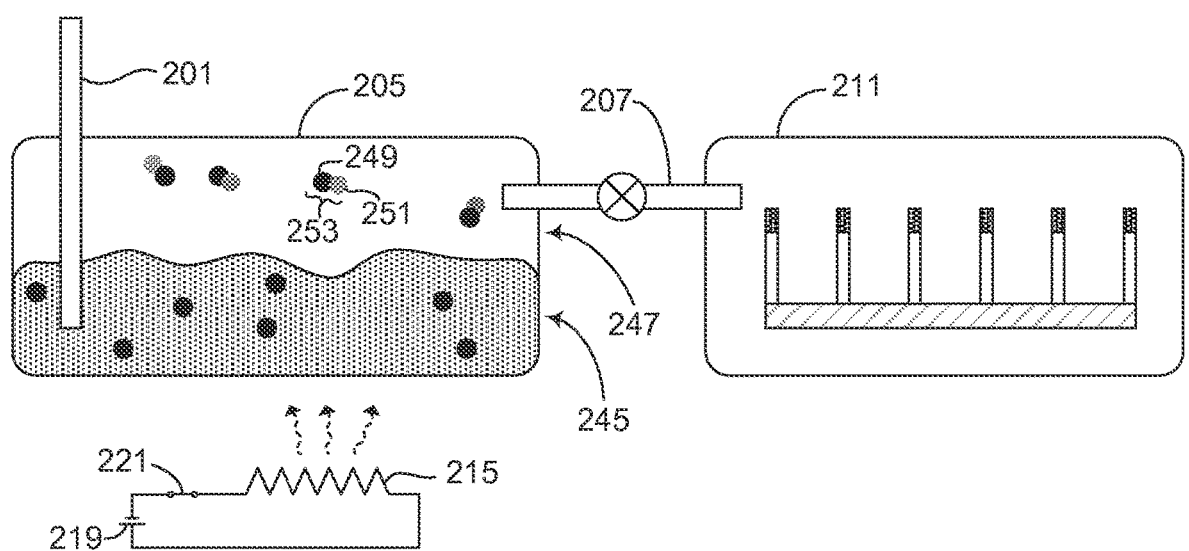
FIG. 4 shows the apparatus of FIG. 2 in which the analyte has mixed with the solvent.

In FIG. 4, the analyte 241 has entered the first chamber 205 through the input port 201 and has mixed with the solvent to form a mixture. Some of the mixture is in liquid phase 245, and some of mixture has evaporated into gas phase 247. In both liquid and gas phases of the mixture, molecules of the analyte such as an analyte molecule 249 have attached to molecules of the solvent such as a solvent molecule 251, forming combinations such as a combination 253. The analyte 241 is shown in the example of FIG. 2 as ready to enter the first chamber 205 in gas phase, but the analyte may be introduced into the first chamber in solid, liquid, or gas phase. It may be bubbled through the solvent, or the analyte and solvent may be mixed in some other way such that solvent molecules attach to analyte molecules.

Applying heat to the first chamber 205, for example by closing the switch 221 to activate the heater 215, causes some of the liquid-phase mixture to evaporate and increases the pressure of the gas-phase mixture, urging the gas-phase mixture through the fluid channel 207 into the second chamber 211. Vaporizing may be aided or induced by reducing pressure in the first chamber. Under suitable conditions of temperature and pressure, the gas-phase mixture may flow into the second chamber without any application of heat or change of pressure in the first chamber.

Transferring the mixture in gas phase from the first chamber to the second chamber has the effect of filtering out any contaminants that remain in solid or liquid phase in the first chamber.

Figure 5:
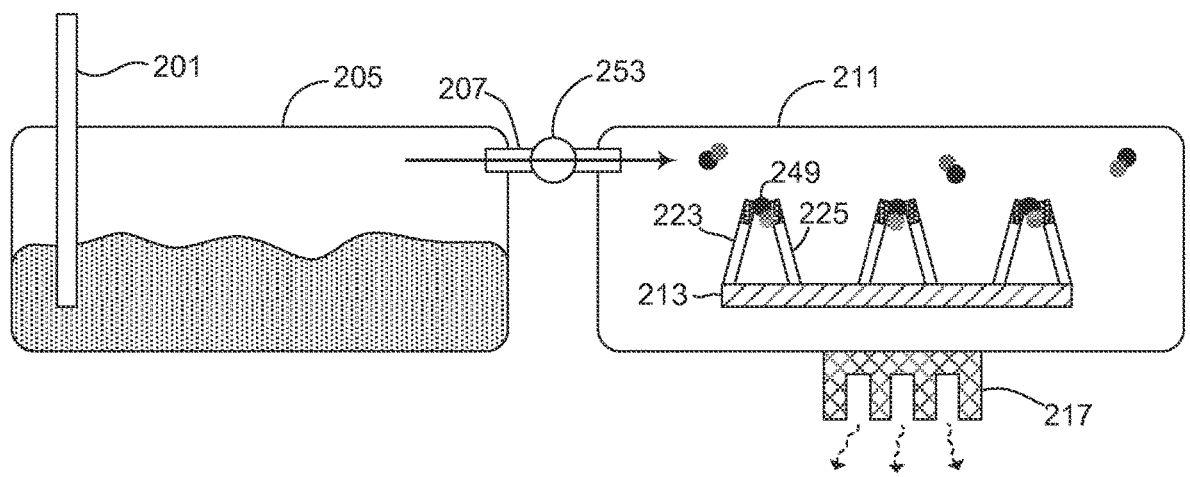
FIG. 5 shows the apparatus of FIG. 4 in which the analyte-solvent mixture has been condensed onto a substrate.

Turning now to FIG. 5, the gas-phase analyte-solvent mixture has moved into the second chamber 211 through the fluid channel 207. Movement of the mixture may be controlled by a valve 253 in the fluid channel 207. The valve may be operated electrically, for example by the computer 301, or manually.

As discussed previously, in some examples movement of the mixture into the second chamber may be facilitated by a temperature differential between the chambers. A temperature differential may be created by heating the first chamber as previously discussed, or by cooling the second chamber as indicated by the heat sink 217 radiating heat away from the second chamber, or by both heating the first chamber and cooling the second.

In some examples a pressure gradient (not shown is created between the chambers instead of, or in addition to, a temperature differential. For example, the first chamber 205 may be positively pressurized. In one application, the analyte comprises a sample of breath from a person suspected of being under the influence of an intoxicant, and the pressure gradient may be generated by the person blowing into the input port 201. Or the substrate may be enclosed in a vacuum package, in which case opening the valve 253 allows the vaporized mixture from the first chamber to enter the second chamber under the influence of the relatively higher pressure in the first chamber.

The gaseous mixture of solvent and analyte condenses on the substrate in the second chamber. Condensation may occur because of a temperature difference between the chambers, for example as a result of using the heating element 215 or the heat sink 217 described above. Condensation may occur because of lower pressure in the second chamber than in the first. In the example shown, capillary forces that result from condensation of the mixture on the nanofingers of the substrate cause the nanofingers to deform toward each other, trapping individual molecules. For example, capillary action has caused the nanofingers 223 and 225 to deform toward each other, trapping the combination 249 of an analyte molecule and a solvent molecule. Or the nanofingers may be arranged in a two-dimensional array such that three, four, or even more nanofingers bend toward each other. If there is a substrate without nanofingers, for example a rough-surface substrate such as the substrate 113 shown in FIG. 1, molecules of analyte and solvent tend to be attracted toward the substrate and adsorbed on its surface more readily than molecules of analyte alone, and therefore the probability of adsorption is increased.

Figure 6:
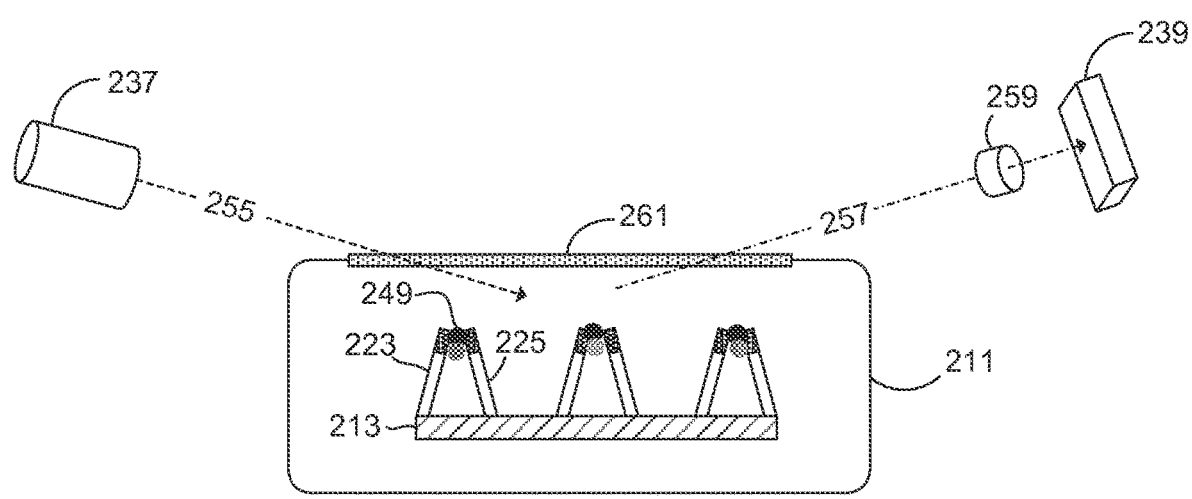
FIG. 6 shows the apparatus of FIG. 5 in which the substrate is exposed to incident radiation to obtain scattered radiation.

Referring to FIG. 6, the laser 237 is shown directing a laser beam 255 at the analyte molecules on the substrate. A scattered beam 257 propagates to the photocell 239. In scattering off the molecules of analyte, wavelengths of some of the photons in the incident beam are shifted as energy is transferred between the photons and the molecules. Photons incident on the photo detector generate corresponding electrical signals that indicate which wavelengths are present.

Additional optical elements may be disposed in the path of the laser beam 255 or in the path of the scattered beam 257. This is indicated generally in FIG. 6 by an optical element 259 in the path of the scattered beam 257. These additional elements may comprise optical filters, light dispersion elements such as gratings, and the like. In the example shown in FIG. 6, the chamber 211 has an optically-transmissive surface 261 through which the laser beam 255 and the scattered beam 257 propagate. In other examples the entire chamber 211 may be made of optically-transmissive material, or one or both of the laser 237 and the photocell 239 may be disposed inside the chamber.

Figure 7:
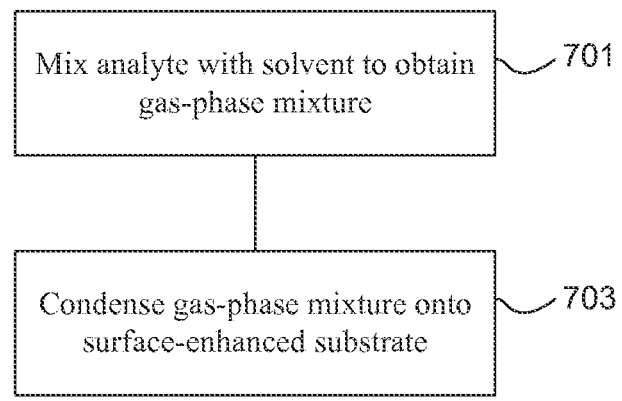
FIG. 7 is a flowchart giving an example of a method of processing an analyte.

An example of a method of processing an analyte is shown in FIG. 7. The analyte is mixed (701) with a solvent to obtain a gas-phase mixture in which analyte molecules are attached to solvent molecules. The mixture is condensed (703) onto a surface-enhanced substrate.

Figure 8:
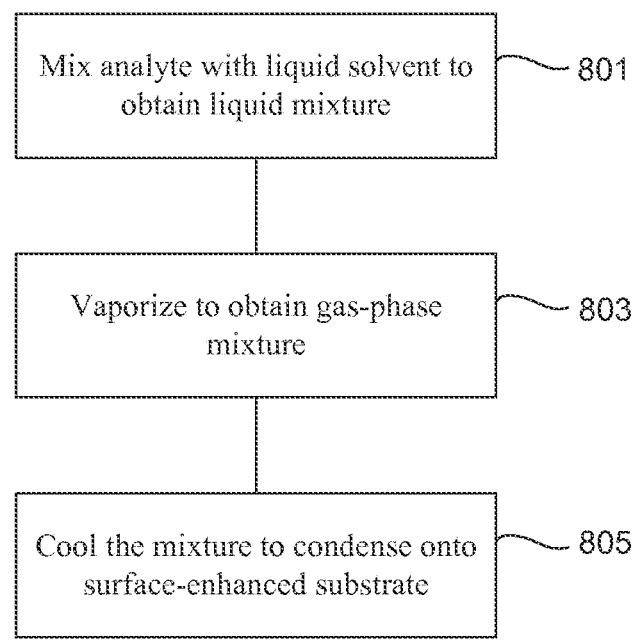
FIG. 8 is a flowchart giving another example of a method of processing an analyte.

Another example of processing an analyte is illustrated in FIG. 8. The analyte is mixed (801) with a liquid solvent to obtain a liquid mixture. The mixture is vaporized (803), for example by applying heat or by partial evacuation, to obtain a gas-phase mixture in which analyte molecules are attached to solvent molecules. The mixture is condensed (805) onto a surface-enhanced substrate, for example by cooling. If the surface-enhanced substrate comprises a plurality of nanofingers, condensing the mixture onto the substrate comprises trapping analyte molecules between groups of the nanofingers. If a substrate having a rough metal surface is used, the mixture is adsorbed onto the substrate, for example by cooling it.

Molecules of analyte in gas phase may be directly trapped or adsorbed onto the substrate without first condensing into liquid phase.

Figure 9:
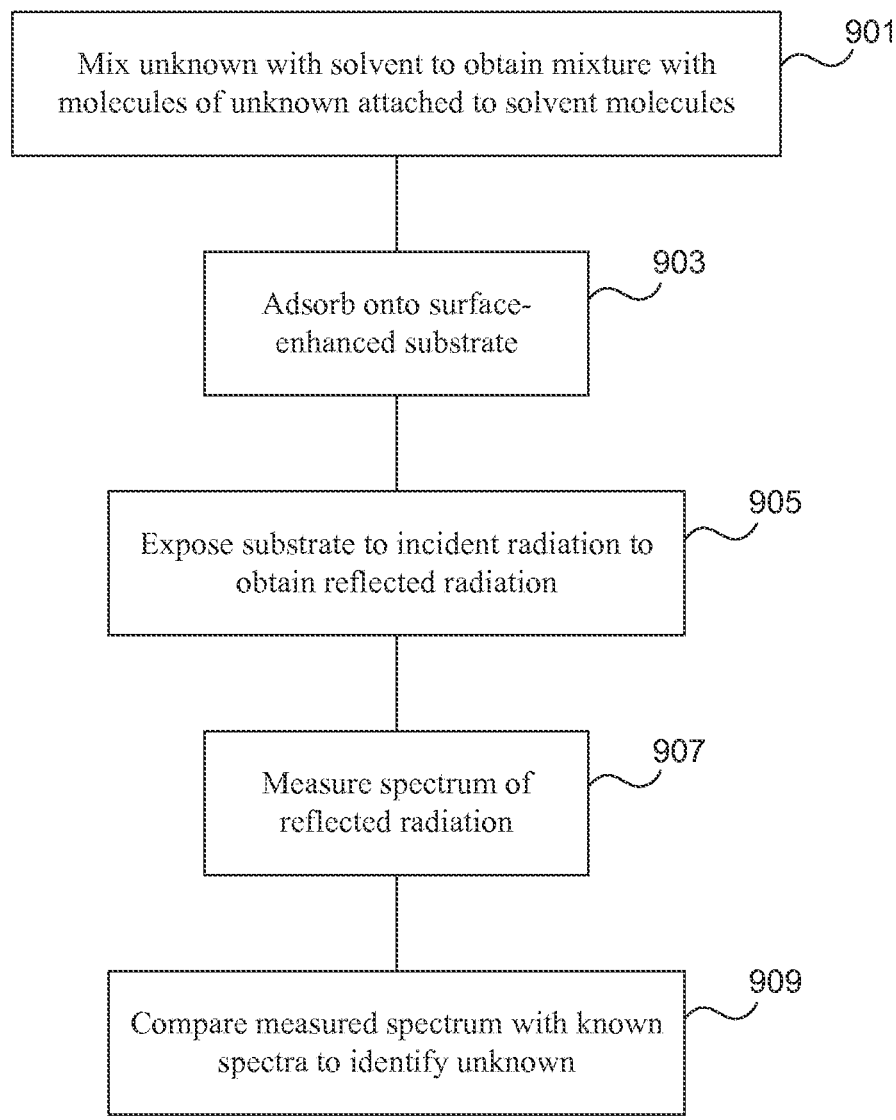
FIG. 9 is a flowchart giving an example of a method of identifying an analyte.

An example of a method of analyzing an unknown substance is illustrated in FIG. 9. The unknown substance is mixed (901) with a solvent to obtain a mixture in which molecules of the unknown substance are attached to molecules of the solvent. The mixture is adsorbed (903) onto a surface-enhanced substrate. The substrate is exposed (905) to incident laser radiation to obtain scattered radiation. A spectrum of the scattered radiation is measured (907) and the measured spectrum is compared (909) with known spectra to identify the unknown substance.

The foregoing approach to analysis of unknown substances enables identification of trace elements in gas, liquid, and solid phases. Identification of gas-phase materials is of interest in many applications, among them detecting explosives and identifying drugs. Pre-filtering is accomplished by passing the analyte through the solvent, minimizing contamination and improving selectivity. This pre-filtering may also filter out unwanted components because materials with low vapor pressure or low solubility will not be carried to the substrate. Substrates can be protected in packaging until actually used, which can aid in prolonging shelf life. SERS spectroscopy systems employing the principles illustrated and described above can be integrated at the micro-scale level to provide compact integrated solutions.

We claim:

1. A molecule sensing apparatus comprising:
   first and second chambers;
   an input port extending into the first chamber;
   a fluid channel extending from the first chamber to the second chamber; and
   a surface-enhanced substrate in the second chamber, the surface-enhanced substrate comprising nano fingers spaced apart and deformable so as to bend towards each other under influence of capillary action resulting from condensation on the nano fingers.

2. The apparatus of claim 1 and further comprising a heater in thermal communication with the first chamber.

3. The apparatus of claim 1 and further comprising a heat sink in thermal communication with the second chamber.

4. The apparatus of claim 1 and further comprising:
   a laser directed toward the substrate; and
   a photo detector oriented to receive laser radiation scattered from the substrate.

5. The apparatus of claim 4 and further comprising a computer in electrical communication with the photo detector, the computer programmed to:
   determine a spectrum according to an output signal from the photo detector;
   compare the spectrum with spectra of known substances; and
   identify the analyte according to the comparison.

6. The apparatus of claim 5 wherein the computer is programmed to:
   determine a magnitude of a voltage at each wavelength in a band of wavelengths;
   normalize the voltage magnitudes; and
   compare the normalized voltage magnitudes with normalized voltage values corresponding with known substances.

7. The apparatus of claim 5 wherein the computer is programmed to subtract spectral points corresponding with spectral points of the solvent from the determined spectrum.

8. A method of processing an analyte, the method comprising:
   mixing the analyte with a liquid solvent in a first chamber to obtain a liquid-phase mixture;
   vaporizing the liquid-phase mixture in the first chamber to obtain a gas-phase mixture in which analyte molecules are attached to solvent molecules;
   transferring the gas-phase mixture out of the first chamber and into a second chamber containing a surface enhanced substrate; and
   condensing the gas-phase mixture onto the surface-enhanced substrate.

9. The method of claim 8 wherein vaporizing the liquid-phase mixture comprises heating the mixture.

10. The method of claim 8 wherein condensing the mixture comprises cooling the mixture.

11. The method of claim 8, wherein the surface enhanced substrate comprises spaced apart and deformable nano fingers and wherein the method further bending the nano fingers towards each other under influence of capillary action resulting from the condensing of the mixture on the nano fingers.

12. The method of claim 8, wherein the mixing of the analyte with the liquid comprises bubbling the analyte through the liquid.

13. A method of analyzing an unknown substance, the method comprising:
mixing the unknown substance with a solvent to obtain a mixture in which molecules of the unknown substance are attached to molecules of the solvent;
adsorbing the mixture onto a surface-enhanced substrate;
exposing the substrate to incident laser radiation to obtain scattered radiation;
measuring a spectrum of the scattered radiation; and
comparing the measured spectrum with known spectra to identify the unknown substance wherein the unknown substance comprises a fluid, the solvent comprises a liquid, and mixing the unknown substance with the solvent comprises bubbling the unknown substance through the solvent.

14. The method of claim 13 and further comprising heating the mixture.

15. The method of claim 13 wherein adsorbing the mixture comprises cooling the mixture.

16. A molecule sensing apparatus comprising:
first and second chambers, the first chamber to contain a liquid;
an input port extending into the first chamber;
a heater to heat the liquid in the first chamber;
a fluid channel extending from the first chamber to the second chamber;
a surface-enhanced substrate in the second chamber;
a laser directed toward the substrate; and
a photo detector oriented to receive laser radiation scattered from the substrate.

17. The apparatus of claim 16 and further comprising a computer in electrical communication with the photo detector, the computer programmed to:
determine a spectrum according to an output signal from the photo detector;
compare the spectrum with spectra of known substances; and
identify the analyte according to the comparison.

18. The apparatus of claim 16 and further comprising a heat sink in thermal communication with the second chamber.

19. The apparatus of claim 16, wherein the laser directs light on to the surface-enhanced substrate and wherein the photodetector receives the light originating from the laser after being scattered by the substrate.

20. The apparatus of claim 16, wherein the input port is located so as to bubble an analyte through the liquid.

* * * * *